United States Patent [19]

Gillman et al.

[11] 4,185,031

[45] Jan. 22, 1980

[54] FLUORINATED PHOSPHINIC ACIDS

[75] Inventors: Hyman D. Gillman, East Vincent Township, Chester County; James P. King, Upper Gwynedd Township, Montgomery County, both of Pa.

[73] Assignee: The United States of America as represented by the Secretary of the Air Force, Washington, D.C.

[21] Appl. No.: 946,265

[22] Filed: Sep. 27, 1978

[51] Int. Cl.$^2$ .......................... C07F 9/30; C10M 1/44
[52] U.S. Cl. ............................ 260/502.4 R; 252/42.7; 260/429.3; 260/429.5; 260/438.5 R; 260/439 R
[58] Field of Search ................................. 260/502.4 R

[56] References Cited

U.S. PATENT DOCUMENTS 3,719,448   3/1973   Chance et al. ................ 260/502.4 R

FOREIGN PATENT DOCUMENTS 1443533   3/1969   Fed. Rep. of Germany .... 260/502.4 R

*Primary Examiner*—Joseph E. Evans
*Attorney, Agent, or Firm*—Joseph E. Rusz; Cedric H. Kuhn

[57] ABSTRACT

Fluorinated phosphinic acids prepared by reaction of fluorinated olefins with an acid containing one or more P-H bonds in the presence of a free radical initiator. The reaction products of the acids with various metal centers are effective grease thickeners for liquid lubricants.

4 Claims, No Drawings

FLUORINATED PHOSPHINIC ACIDS

RIGHTS OF THE GOVERNMENT

The invention described herein may be manufactured and used by or for the Government of the United States for all governmental purposes without the payment of any royalty.

FIELD OF THE INVENTION

This invention relates to fluorinated phosphinic acids. In one aspect it relates to a process for synthesizing the fluorinated phosphinic acids. In another aspect it relates to grease thickeners for various fluids and to grease compositions containing the thickener.

BACKGROUND OF THE INVENTION

In the past, inorganic polymers have been added to various fluids to obtain grease compositions. For example, as disclosed in U.S. Pat. No. 3,332,873, greases are made frm phosphate esters by the addition of certain inorganic polymers which contain double phosphinate bridges and two unidentate ligands. According to U.S. Pat. No. 3,331,774, a diester liquid is converted to a grease by addition of similar inorganic polymers. U.S. Pat. No. 3,331,775 discloses that silicone fluids are converted to greases by adding a relatively low molecular weight doubly bridged chromium phosphinate polymer. And in U.S. Pat. No. 3,522,178, it is revealed that grease compositions can be formulated by using triply bridged chromium atoms where the bridging groups are the anions of phosphinic acids. While the prior art discloses effective thickeners for various fluids, there is a need for polymers that are especially adapted for thickening to a grease-like consistency synthetic fluids containing fluorinated and perfluorinated groups.

It is a principal object of this invention, therefore, to provide fluorinated phosphinic acids which can be reacted with various metal centers to provide thickeners for synthetic fluids containing fluorinated and perfluorinated groups.

Another object of the invention is to provide a process for synthesizing the fluorinated phosphinic acids.

A further object of the invention is to provide polymers that are effective grease thickeners for various high temperature fluids.

Still another object of the invention is to provide grease compositions based on a liquid lubricant thickened with an inorganic polymer obtained by reacting the fluorinated phosphinic acids with various metal centers.

Other objects and advantages of the invention will become apparent to those skilled in the art upon consideration of the accompanying disclosure.

SUMMARY OF THE INVENTION

The present invention resides in a fluorinated phosphinic acid having the following formula:

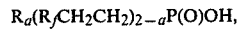

wherein R is alkyl or aryl; $R_f$ is a perfluoroalkyl; and a is zero or 1. The R group generally contains about 1 to 12 carbon atoms, examples of which include methyl, ethyl, t-butyl, hexyl, octyl, decyl, dodecyl, phenyl, tolyl, xylyl, naphthyl, and the like. The $R_f$ group is a straight or branched chain perfluoroalkyl group containing about 1 to 30 carbon atoms, i.e., a $C_nF_{2n+1}$ group where n is from about 1 to 30. Examples of such a group include $(CF_3)_2CF(CF_2CF_2)_x$ where x is zero or an integer from 1 to 4, inclusive.

In one embodiment, the present invention lies in a process for synthesizing the fluorinated phosphinic acids. In accordance with this process, the acids are prepared by reacting fluorinated olefins with an acid containing one or more P-H bonds in the presence of a free radical initiator. The reactions involved in the synthesis can be represented by the following formulas:

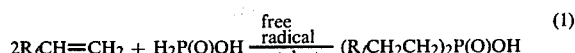

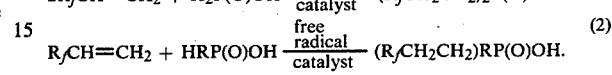

In the foregoing equations, R and $R_f$ are as defined hereinabove.

As shown by the above equations, the fluroinated phosphinic acids are prepared by reacting a fluorinated olefin with a phosphinic acid in the presence of a free radical catalyst. The free radical catalyst used is of the peroxide type, such as benzoyl peroxide and t-butyl perpivalate. It is often preferred to employ t-butyl perpivalate as the catalyst. The reaction is carried out in a solvent under a blanket of an inert gas, such as nitrogen, argon or helium, at a temperature ranging from about 70° to 80° C. It is usually preferred to utilize t-butyl alcohol as the solvent. A mole ratio of phosphinic acid to fluorinated olefin of 1:1 is used when preparing $(R_fCH_2CH_2)RP(O)OH$. When preparing $(R_fCH_2CH_2)_2P(O)OH$, a 1:2 mole ratio of phosphinic acid to fluorinated olefin is employed. The fluorinated olefin and phosphinic acid reactants used in the process are well known compounds that are described in the literature.

The fluorinated phosphinic acids are useful in preparing thickeners for various fluids, particularly those of a synthetic nature containing fluorinated and perfluorinated groups. Thus, in another embodiment, the present invention relates to poly(metal phosphinate) grease thickeners which are the reaction products of the fluorinated acids with different metal centers. The poly(metal phosphinates) can be represented by the following formulas:

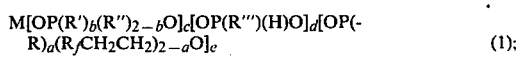

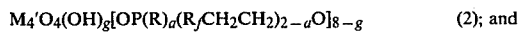

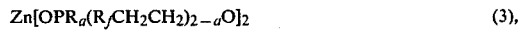

wherein M is trivalent chromium or iron, M' is tetravalent titanium, zirconium or hafnium, R is alkyl or aryl, $R_f$ is perfluoroalkyl, R', R" and R‴ are alkyl or aryl, a and b are each zero or 1, c and d each range from zero to 3 and e ranges from 0.1 to 3, with any one of c, d and e equaling 2 or the sum of any two of c, d and e equaling 2, and the sum of c, d and e equaling 3, and g ranges from zero to 7.9. Like the R group described above, the R', R", and R‴ groups usually contain about 1 to 12 carbon atoms while the $R_f$ group is a straight or branched chain perfluoroalkyl containing about 1 to 30 carbon atoms.

The poly(metal phosphinate) according to formula (1) above is synthesized by initially preparing a polymeric chromium (or iron) bisphosphinate in accordance with the procedure described by H. D. Gillman et al in Inorganic Syntheses, XVI, 89–92 (1976). As disclosed in this publication, a solution of a phosphinic acid and potassium carbonate in water-tetrahydrofuran is added with stirring to a solution of a soluble simple chromium salt, such as chromium chloride. The phosphinic acid has the formula $R_b'R''_{2-b}P(O)OH$, $R'''(H)P(O)OH$ or $R_a(R_fCH_2CH_2)_{2-a}P(O)OH$ where R, $R_f$, R', R'', R''', a, and b are as defined above, or a mixture of the phosphinic acids. The mole ratio of phosphinic acid or mixture of phosphinic acids to the chromium salt is 2:1. The resulting mixture is brought to a boil and the tetrahydrofuran is allowed to evaporate. After most of the tetrahydrofuran has evaporated, additional water is added. Boiling is continued until a precipitate is formed that can be readily ground with a spatula. The precipitate is then separated, thoroughly washed with water, and then allowed to dry. The water-containing polymer obtained is then heated under a vacuum to constant weight, thereby converting it to a hydroxobis(phosphinate)polymer. The bisphosphinate polymer is then reacted in a low boiling solvent, such as chloroform, with one mole of one of the aforementioned phosphinic acids or a mixture of the acids to form a gel of a chromium tris(phosphinate)polymer in the solvent. It is to be understood that a fluorinated phosphinic acid of this invention is used in preparing the bisphosphinate or in the preparation of this trisphosphinate by reaction with the bisphosphinate. After standing for 15 to 60 minutes, the gel forms a viscous solution of the chromium tris(phosphinate)polymer.

When preparing a grease composition using the poly[chromium (or iron) phosphinate] of formula (1) as the thickener, the viscous solution mentioned in the preceding paragraph is added to a liquid lubricant. The resulting mixture is then stirred while heating to a temperature of about 120° C. whereby the solvent is evaporated and a grease is formed. The grease is then cured by heating at a temperature ranging from about 150° to 250° C. for a period of about 1 to 2 hours.

The poly(metal phosphinates) according to formula (2) above are synthesized directly in the liquid lubricant to be thickened to a grease composition. Initially, zirconium oxychloride ($ZrOCl_2.8H_2O$) or the corresponding titanium or hafnium compound, is dissolved in distilled water and then hydrolyzed with an ammonium hydroxide solution. After washing with distilled water, the wet hydrolyzed solid $[ZrO(OH)_{2.xH_2O}]$ is then reacted at a temperature between 80° and 110° C. with a fluorinated phosphinic acid of this invention dispersed in the liquid lubricant to be thickened. The reaction mixture is continuously stirred for a period of about 60 minutes while being maintained at a temperature of about 110° C. During this heating period, any water separating from the reaction mixture is decanted off. The poly(metal phosphinate) that forms thickens the liquid lubricant to a grease-like consistency. The grease is cured by heating at a temperature ranging from about 150° to 250° C. for a period of about 1 to 2 hours. The composition of the thickener can be varied by controlling the mole ratio of the zirconyl hydroxide $[ZrO(OH)_2]$ to fluorinated phosphinic acid. The mole ratio of zirconyl hydroxide to fluorinated phosphinic acid can range from 1:1 to 8:1.

In synthesizing the poly(metal phosphinates) according to formula (3) above, a fluorinated phosphinic acid of this invention is first neutralized. This is accomplished by treating the acid with a stoichiometric amount of potassium carbonate (0.5 mole per mole of acid) in a methanol-water mixture. (An excess of potassium carbonate is avoided in order to prevent the formation of zinc hydroxy phosphinates in the next step of the process.) The potassium phosphinate solution is then added slowly with stirring to an aqueous solution of zinc sulfate. The mole ratio of potassium phosphinate to zinc sulfate is 0.5:1. After completion of the addition, the solution is heated to boiling and maintained thereat until all of the methanol is removed. The precipitate that forms, i.e., the poly(zinc phosphinate), is then recovered, e.g., by filtration, washed with water, and dried in a vacuum desiccator.

In general, a thickening amount of the poly(metal phosphinates) as described above is used with a liquid lubricant to provide a grease composition. It will be understood that the precise amount utilized depends upon the desired final viscosity of the grease. The amount of the thickening agent is usually in the range of 6 to 35 weight percent, preferably 8 to 30 weight percent, based upon the weight of the grease composition.

The poly(metal phosphinates) can be used as thickening agents for any of the well known liquid lubricants described in the literature. For example, the polymers can be used to thicken silicone fluids, such as a liquid polyorganosiloxane having a high phenyl content and diphenylmethylsilyl end groups. Other silicone fluids, such as poly(methylphenylsiloxane) (Dow Corning 550 lubricant) can also be used. The poly(metal phosphinates) are particularly useful as thickeners for fluorinated fluids, such as perfluoroalkylpolyether fluids. Because of the presence of fluorinated groups substituted on the phosphorus atoms of the poly(metal phosphinates), the compatability between the thickeners and the fluorinated fluid is outstanding. A description of silicone and perfluoroalkylpolyether fluids is given in "Non-Hydrocarbon Liquid Lubricant Technology" by Herbert Schwenker in Assessment of Lubricant Technology, published by American Society of Mechanical Engineers, 89–99(1972). Perfluoroalkylethers are also described in "PR-143, A New Class of High Temperature Fluids", ASLE Trans. 9, 24–30(1966).

A more comprehensive understanding of the invention can be obtained by referring to the following illustrative examples which are not intended, however, to be unduly limitative of the invention.

EXAMPLE I

Preparation of $(CF_3)_2CF(CF_2)_4CH_2CH_2(C_6H_5)P(O)OH$

In a nitrogen atmosphere, a solution containing 0.3 g t-butyl perpivalate in 60 ml of t-butyl alcohol was dropped slowly into a solution containing phenylphosphinic acid (14.0 g, 0.099 mole) and $(CF_3)_2CF(CF_2)_4CH=CH_2$ (40.0 g, 0.10 mole) in 250 ml of t-butyl alcohol at 70°–80° C. This addition took 8 hours after which the solution was allowed to reach room temperature. To ensure complete reaction another similar quantity of t-butyl perpivalate solution was added over 4 hours using the same reaction conditions. The solution was again allowed to cool to room temperature and then 150 ml of 6N HCl was added. The resultant white precipitate was filtered off and recrystallized in toluene/ethanol. Elemental analysis confirmed that the product was the fluorinated phosphinic having the formula shown above.

Analysis: Calc'd for $C_{15}H_{10}F_{15}O_2P$: C,33.4; H,1.87. Found: C,31.9; H,2.16.

EXAMPLE II

Preparation of $(CF_3)_2CF(CF_2)_6CH_2CH_2(C_6H_5)P(O)OH$

Following a procedure similar to that described in Example I, $(C_6H_5)$ (H)P(O)OH (14.2 g, 0.1 mole) was allowed to react with $(CF_3)_2CF(CF_2)_6CH=CH_2$ in the presence of t-butyl perpivalate. Elemental analysis confirmed that the product was the fluorinated phosphinic acid having the formula shown above.

Analysis: Calc'd for $C_{17}H_{10}F_{19}O_2P$: C,32.0; H,1.58; P,5.0. Found: C,32.0; H,1.78; P,4.6.

EXAMPLE III

Preparation of $[(CF_3)_2CF(CF_2)_4CH_2CH_2]_2P(O)OH$

The same procedure used in Example I was followed for the preparation of $[(CF_3)_2CF(CF_2)_4CH_2CH_2]_2P(O)OH$, utilizing $(CF_3)_2CF(CF_2)_4CH=CH_2$ and $H_2P(O)OH$ as the reactants. However, this reaction was run for 3-4 days with constant slow addition of the t-butyl perpivalate solution. The total t-butyl perpivalate used for the reaction was 2-3 grams with 0.1 mole of the reactants. Elemental analysis confirmed that the product was the fluorinated phosphinic acid having the foregoing formula.

Analysis: Calc'd for $C_{18}H_9F_{30}O_2P$: C,25.2; H,1.06. Found: C,22.4; H,1.44.

EXAMPLE IV

Preparation of $Zn\{OP[CH_2CH_2(CF_2)_6CF(CF_3)_2]_2O\}_2$

The fluorinated phosphinic acid $[(CF_3)_2CF(CF_2)_6CH_2CH_2]_2P(O)OH$ was prepared in the manner described in Example I, utilizing $(CF_3)_2CF(CF_2)_6CH=CH_2$ and $H_2P(O)OH$ as the reactants. The phosphinic acid was neutralized by treating it with a stoichiometric amount of $K_2CO_3$ in a methanol-water mixture (0.5 mole of $K_2CO_3$ per mole of acid). The solution of potassium phosphinate obtained, namely, $K\{OP[CH_2CH_2(CF_2)_6CF(CF_3)_2]_2\}_2$ was then added slowly with stirring to an aqueous solution of zinc sulfate (2 moles potassium phosphinate per mole of $ZnSO_4.7H_2O$). After completion of the addition, the solution was heated so as to boil off the methanol. The precipitate that formed was recovered by filtration, washed with water, and dried in a vacuum desiccator. Elemental analysis confirmed that the product was the zinc bis(phosphinate) having the above formula.

Analysis: Calc'd for $C_{44}H_{16}F_{76}O_4P_2Zn$: C,24.2; H,0.7; P,2.84. Found: C,24.9; H,1.2; P,2.8.

EXAMPLE V

A series of runs was conducted in which the procedure described in Example IV was followed in preparing the following zinc bis(phosphinates):

(1) $ZN\{OP[(CH_2CH_2) (CF_2)_4CF(CF_3)_2]C_6H_5O\}_2$
(2) $Zn\{OP[(CH_2CH_2) (CF_2)_6CF(CF_3)_2]C_6H_5O\}_2$
(3) $Zn\{OP[(CH_2CH_2) (CF_2)_4CF(CF_3)_2]_2O\}_2$.

The following fluorinated phosphinic acids were used in synthesizing the bisphosphinates:

(1) $(CF_3)_2CF(CF_2)_4CH_2CH_2(C_6H_5)P(O)OH$,
(2) $(CF_3)_2CF(CF_2)_6CH_2CH_2(C_6H_5)P(O)OH$
(3) $[(CF_3)_2CF(CF_2)_4CH_2CH_2]P(O)OH$.

Elemental analysis of the three zinc bis(phosphinates) gave the following results:

(1) Calc'd for $C_{30}H_{18}F_{30}O_4P_2Zn$: C,31.6; H,1.59; P,5.44. Found: C,31.5; H,1.87, P,5.75.
(2) Calc'd for $C_{34}H_{18}F_{38}O_4P_2Zn$: C,30.5; H,1.35. Found: C,30.4; H,1.58.
(3) Calc'd for $C_{36}H_{16}F_{60}O_4P_2Zn$: C,24.3; H,0.91; P,3.48. Found: C,24.5; H,1.13; P,2.8.

EXAMPLE VI

A series of runs was conducted in which greases were prepared from various liquid lubricants, utilizing the following poly(metal phosphinates) as thickening agents:

(A) $Cr[OP(Me)(Ph)O]_2[OP(Ph)(H)O]_{0.5}[OP(Ph)(CH_2CH_2C_9F_{19})O]_{0.5}$,
(B) $Zr_4O_4(OH)_{7.5}[OP(CH_2CH_2C_9F_{19})_2O]_{0.5}$,
(C) $Zr_4O_4(OH)_7[OP(Ph)(CH_2CH_2C_9F_{19})O]$, and
(D) $Zr_4O_4(OH)_{7.5}[OP(Ph)(CH_2CH_2C_9F_{19})O]_{0.5}$.

The thickening agents and greases were prepared according to the procedures described hereinabove. In the case of thickening agent (A), a mixture of $Cr[OP(Me)(Ph)O]_2OH$ [prepared by the procedure described in Inorganic Syntheses, XVI, 89(1976)], (Ph(H)P(O)OH, and $(CF_3)_2CF(CF_2)_6CH_2CH_2(C_6H_5)P(O)OH$ in a 1:0.5:0.5 mole ratio was suspended in $CHCl_3$, resulting initially in the formation of a gel which subsequently became a viscous solution. The solution was added to the liquid lubricant which was heated with stirring to evaporate the solvent and form a grease. The grease was cured at an elevated temperature and milled several times on a three-roll mill.

In the case of thickening agents (B), (C) and (D), the poly(zirconium fluorinated phosphinates) were synthesized directly in the liquid lubricant to be thickened. Initially, in preparing each thickener, zirconium oxychloride $(ZrOCl_2.8H_2O)$ was dissolved in distilled water and then hydrolyzed with a 1N $NH_4OH$ solution. The wet hydrolyzed solid $(ZrO(OH)_2).xH_2O$ after being washed several times with distilled water was reacted with $[(CF_3)_2CF(CF_2)_6CH_2CH_2]_2P(O)OH$ (B) or $(CF_3)_2CF(CF_2)_6CH_2CH_2(C_6H_5)P(O)OH$ (C and D) dispersed in a liquid lubricant between 80° and 110° C. The reaction mixture was then stirred while heating to provide a grease which was heated to a constant weight and then milled several times on a roll mill. The mole ratios of zirconium oxychloride to fluorinated acid used in preparing the thickeners were as follows: 8:1(B), 4:1(C), and 8:1(D).

The results obtained in evaluating the greases are shown hereinafter in the table.

TABLE

| | A | B | C | D |
|---|---|---|---|---|
| Fluid | Polysiloxane | Perfluoroalkyl polyether | Perfluoroalkyl polyether | Fluorinated Polysiloxane |
| Thickener | (1) | (2) | (3) | (4) |
| Wt % Thickener | 8 | 30 | 30 | 30 |

| | A | B | C | D |
|---|---|---|---|---|
| Penetration (ASTM D 1403) | | | | |
| Unworked (Conv to D 217) | 275 | 238 | 279 | 174 |
| Worked (Conv to D 217) | 286 | 260 | 237 | 215 |
| Drop Point (ASTM D 566), °F. | 435 | >464 | 454 | >464 |
| Oil Separation (FTMS 791-321) Wt % after 30 h at 400° F. | 22 | 4.0 | 5.4 | 1.0 |
| Oxidation Stability (ASTM D 942) Psig $O_2$ Pressure Drop in 600 h, 210° F. | 0 | 0 | 0 | 0 |
| Extreme Pressure Properties (ASTM D 2596) | | | | |
| Weld Point, kg (AISI-C-52100 steel) | 250 (125)[5] | 470 (400) | >620 (400) | 200 (125) |
| Wear Prevention Characteristics (ASTM D 2266) 40 kg load, 1200 rpm, 167° F. and 1 h | | | | |
| Scar diameter, mm (AISI-C-52100 steel) | 3.58 (3.75)[5] | 0.49 (1.09) | 0.56 (1.09) | 1.52 (1.26) |

[1] $Cr[OP(Me)(Ph)O]_2[OP(Ph)(H)O]_{0.5}[OP(PH)(CH_2CH_2C_9F_{19})O]_{0.5}$.
[2] $Zr_4O_4(OH)_{7.5}[OP(CH_2CH_2C_9F_{19})_2O]_{0.5}$.
[3] $Zr_4O_4(OH)_7[OP(PH)(CH_2CH_2C_9F_{19})O]$.
[4] $Zr_4O_4(OH)_{7.5}[OP(Ph)(CH_2CH_2C_9F_{19})O]_{0.5}$.
[5] Data in parentheses are for the base fluids.

As seen from the foregoing data, liquid lubricants thickened with poly(metal fluorinated phosphinates) based on the fluorinated phosphinic acids of this invention provide grease compositions possessing outstanding properties. In particular, the grease compositions demonstrate outstanding properties with respect to thickener-fluid compatability, oxidation stability, oil separation, drop point, and performance results, such as wear prevention characteristics and load carrying capacity.

As will be evident to those skilled in the art, modifications of the invention can be made in view of the foregoing disclosure without departing from the spirit and scope of the invention.

We claim:
1. A fluorinated phosphinic acid having the following formula:

$$R(R_fCH_2CH_2)P(O)OH,$$

wherein R is alkyl or aryl and $R_f$ is perfluoroalkyl.

2. The fluorinated phosphinic acid according to claim 1 in which R is aryl, and $R_f$ is $(CF_3)_2CF(CF_2CF_2)_x$, where x is zero or an integer from 1 to 4, inclusive.

3. The fluorinated phosphinic acid according to claim 2 in which R is phenyl and $R_f$ is $(CF_3)_2CF(CF_2)_4$.

4. The fluorinated phosphinic acid according to claim 2 in which R is phenyl and $R_f$ is $(CF_3)_2CF(CF_2)_6$.